US012797010B2

(12) United States Patent
Kuan et al.

(10) Patent No.: US 12,797,010 B2
(45) Date of Patent: Nov. 17, 2026

(54) PHOTOPLETHYSMOGRAPHY FRONT-END RECEIVER, CAPACITIVE TRANSIMPEDANCE AMPLIFYING DEVICE, AND METHOD FOR SAMPLING SIGNAL

(71) Applicant: REALTEK SEMICONDUCTOR CORPORATION, Hsinchu (TW)

(72) Inventors: Ming-Chih Kuan, Hsinchu (TW); Tzu-Hsuan Yang, Hsinchu (TW); Liang-Hui Li, Hsinchu (TW)

(73) Assignee: REALTEK SEMICONDUCTOR CORPORATION, Hsinchu (TW)

( * ) Notice: Subject to any disclaimer, the term of this patent is extended or adjusted under 35 U.S.C. 154(b) by 851 days.

(21) Appl. No.: 18/196,587

(22) Filed: May 12, 2023

(65) Prior Publication Data

US 2023/0363717 A1 Nov. 16, 2023

Related U.S. Application Data

(60) Provisional application No. 63/342,170, filed on May 16, 2022.

(51) Int. Cl.
*A61B 5/00* (2006.01)
*A61B 5/024* (2006.01)

(52) U.S. Cl.
CPC ........ *A61B 5/7203* (2013.01); *A61B 5/02416* (2013.01); *A61B 5/7225* (2013.01)

(58) Field of Classification Search
CPC .. A61B 5/7203; A61B 5/02416; A61B 5/7225
See application file for complete search history.

(56) References Cited

U.S. PATENT DOCUMENTS 9,717,424 B2 * 8/2017 Kulach .............. A61B 5/02405
10,624,542 B2 * 4/2020 Richards .............. A61B 5/7214
2023/0102504 A1 3/2023 Li

FOREIGN PATENT DOCUMENTS

CN 108606801 A 10/2018

OTHER PUBLICATIONS

Wong et al. Low-Power CMOS Front-End for Photoplethysmographic Signal Acquisition With Robust DC Photocurrent Rejection. (Year: 2008).*

(Continued)

*Primary Examiner* — Lina Cordero
*Assistant Examiner* — Lynda Dinh
(74) *Attorney, Agent, or Firm* — WPAT, PC

(57) ABSTRACT

A method for sampling a signal can accurately cancel a noise signal. The method is performed by a capacitive transimpedance amplifying device that can be applied to a photoplethysmography front-end receiver. The method includes sampling a detection signal and its inversion several times in specific order in a sampling period to obtain a target signal without a noise signal. Specifically, the method includes: sampling the detection signal during a first time slot and a fourth time slot; and sampling the inversion of the detection signal during a second time slot and a third time slot, wherein the first, second, third, and fourth time slots are in sequence and included in the sampling period, the detection signal includes the target signal and the noise signal during the first and fourth time slots, and the detection signal only includes the noise signal during the second and third time slots.

20 Claims, 6 Drawing Sheets

(56) References Cited

OTHER PUBLICATIONS

Lin et al. 14.85 uW Analog Front-End for Photoplethysmography Acquisition with 142-dBW Gain and 64.2-pArms Noise. (Year: 2019).*
Lin et al. "A 119dB Dynamic Range Charge Counting Light-to-Digital Converter for Wearable PPG_NIRS Monitoring Applications(clear version)" Aug. 2020, IEEE.
Konijinenburg et al. "A_Multibiosensor_Acquisition_System_With_Integrated_Processor_Power_Management_8_times_8_LED_Drivers_and_Simultaneously_Synchronized_ECG_BIO-Z_GSR_and_Two_PPG_Readouts", Nov. 2016, IEEE.
Analog Devices, Inc., "Multimodal sensor front end adpd4100-4101(clear version)", 2020, Analog Devices, Inc.
Texas Instruments "afe4404 Ultra-small, Integrated AFE for wearable, optical, heart-rate monitoring and bio-sensing (clear version)", Jun. 2015, Texas Instruments.
OA letter of a counterpart CN application (appl. No. 202210927002.X) mailed on Feb. 7, 2026.
Shoji Kawahito et al. "Column Parallel Signal Processing Techniques for Reducing Thermal and RTS Noises in CMOS Image Sensors", Jan. 2007, Proceedings of International Image Sensors Workshop (IISW).

* cited by examiner

PHOTOPLETHYSMOGRAPHY FRONT-END RECEIVER, CAPACITIVE TRANSIMPEDANCE AMPLIFYING DEVICE, AND METHOD FOR SAMPLING SIGNAL

BACKGROUND OF THE INVENTION

1. Field of the Invention

The present disclosure relates to signal sampling, especially to a Photoplethysmography (PPG) front-end receiver, a capacitive transimpedance amplifying device, and a signal sampling method that are capable of sampling a detection signal multiple times and sampling the inversion of the detection signal multiple times during a sampling period.

2. Description of Related Art

The photoplethysmography (PPG) technology involves illuminating skin with a controllable light source (e.g., a light emitting diode (LED)) and detecting the reflection light to measure the variation in optical absorption. The PPG technology can be applied to multiple kinds of applications (e.g., the measurement of heartbeat and blood oxygen). However, in addition to the controllable light source, other light sources (e.g., sunlight and indoor light) usually exist in the same space, and the influence of these light sources (hereinafter referred to as "ambient light") should be eliminated to ensure the accuracy of the measurement of the variation in optical absorption. The influence of the ambient light can be eliminated with one of the following technologies:

(1) sampling a PPG signal during a first time interval and sampling an ambient-light signal during a second time interval, and performing analog-to-digital conversion to the sampled PPG signal and the sampled ambient-light signal to generate a digital value of the sampled PPG signal and a digital value of the sampled ambient-light signal respectively, wherein the PPG signal includes an artificial-light signal (e.g., an LED light signal) and an ambient-light signal; afterwards, subtracting the digital value of the sampled ambient-light signal from the digital value of the sampled PPG signal to eliminate the ambient-light component from the digital value of the sampled PPG signal. This technology is named "digital correlated double sampling (DCDS)" and has the following problems:

(i) the DCDS technology cannot eliminate the ambient-light component accurately because the ambient light in the first time interval and the ambient light in the second time interval may be significantly different when the ambient light changes very fast; and (ii) the DCDS technology performs analog-to-digital conversion two times and thus consumes more energy.

The DCDS technology is found in the following document: TEXAS INSTRUMENTS, "AFE4404 Ultra-Small, Integrated AFE for Wearable, Optical, Heart-Rate Monitoring and Bio-Sensing", SBAS689D—JUNE 2015—REVISED DECEMBER 2016.

(2) sampling a PPG signal and an ambient-light signal in a correlated double sampling (CDS) manner in an analog domain, and subtracting the sampled ambient-light signal from the sampled PPG signal in the analog domain to eliminate the ambient-light component from the sampled PPG signal. This technology has the following problems:

(i) when the ambient light changes fast in some circumstances (e.g., a circumstance that a wearable PPG device cannot closely adhere to skin due to user's violent action), this technology cannot eliminate the ambient-light component from the sampled PPG signal accurately.

The above-mentioned technology is found in the following document: Mario Konijnenburg, Member, IEEE, Stefano Stanzione, Member, IEEE, Long Yan, Member, IEEE, Dong-Woo Jee, Member, IEEE, Julia Pettine, Roland van Wegberg, Hyejung Kim, Chris van Liempd, Ram Fish, James Schuessler, Harmke de Groot, Member, IEEE, Chris Van Hoof, Refet Firat Yazicioglu, and Nick Van Helleputte, Member, IEEE, "A Multi(bio)sensor Acquisition System With Integrated Processor, Power Management, 8×8 LED Drivers, and Simultaneously Synchronized ECG, BIO-Z, GSR, and Two PPG Readouts", IEEE JOURNAL OF SOLID-STATE CIRCUITS, VOL. 51, NO. 11, NOVEMBER 2016.

SUMMARY OF THE INVENTION

An object of the present disclosure is to provide a Photoplethysmography (PPG) front-end receiver, a capacitive transimpedance amplifying device, and a signal sampling method which can cancel an ambient-light signal/noise signal accurately.

An embodiment of the PPG front-end receiver of the present disclosure can sample a detection signal multiple times and sampling the inversion of the detection signal multiple times in predetermined sampling sequence during a sampling period to cancel an ambient-light signal of the detection signal and thereby obtain a controllable-light signal of the detection signal, wherein the detection signal is generated by a photoelectric device. This embodiment includes a first capacitive transimpedance amplifier (CTIA). The first CTIA includes a first operational amplifier (OP), a first capacitor, a first switch, a second switch, a third switch, and a fourth switch.

Regarding the above embodiment, the first OP includes a first input node, a first inverting input node, and a first output node, wherein the first input node is for receiving a first reference voltage and the first inverting input node is for receiving the detection signal. The first capacitor includes a first electrode and a second electrode. The first switch is set between the first electrode and the first inverting input node, and the second switch is set between the second electrode and the first output node. The first switch and the second switch are scheduled to be turned on in a first time slot, to be turned off in a second time slot, to be turned off in a third time slot, and to be turned on in a fourth time slot; accordingly, the first electrode and the second electrode of the first capacitor are coupled with the first inverting input node and the first output node respectively during the first time slot and the fourth time slot to allow the first capacitor to sample the detection signal during the first time slot and the fourth time slot, wherein the first time slot, the second time slot, the third time slot, and the fourth time slot are four consecutive time slots included in the sampling period. The third switch is set between the second electrode and the first inverting input node, and the fourth switch is set between the first electrode and the first output node. The third switch and the fourth switch are scheduled to be turned off in the first time slot, to be turned on in the second time slot, to be turned on in the third time slot, and to be turned off in the fourth time slot; accordingly, the second electrode and the first electrode of the first capacitor are coupled with the first inverting input node and the first output node respectively during the second time slot and the third time slot to allow the first capacitor to sample the inversion of the detection signal during the second time slot and the third time slot. The detection signal includes the controllable-light signal and the ambient-light signal during the first time slot and the fourth time slot, and the detection signal includes the ambient-light signal but does not include the controllable-light signal during the second time slot and the third time slot.

An embodiment of the capacitive transimpedance amplifying device of the present disclosure is the aforementioned first CTIA which can sample a detection signal multiple times and sampling the inversion of the detection signal multiple times in predetermined sampling sequence during a sampling period to cancel a noise signal of the detection signal and thereby obtain a target signal of the detection signal.

An embodiment of the signal sampling method of the present disclosure is performed with a capacitive transimpedance amplifying device. This embodiment is used for sampling a detection signal multiple times and sampling the inversion of the detection signal multiple times in predetermined sampling sequence during a sampling period to cancel a noise signal of the detection signal and thereby obtain a target signal of the detection signal. This embodiment includes the following steps: sampling the detection signal instead of the inversion of the detection signal during a first time slot and a fourth time slot; and sampling the inversion of the detection signal instead of the detection signal during a second time slot and a third time slot, wherein the first time slot, the second time slot, the third time slot, and the fourth time slot are four consecutive time slots included in the sampling period, the detection signal includes the target signal and the noise signal during the first time slot and the fourth time slot, and the detection signal includes the noise signal but does not include the target signal during the second time slot and the third time slot.

These and other objectives of the present invention will no doubt become obvious to those of ordinary skill in the art after reading the following detailed description of the preferred embodiments that are illustrated in the various figures and drawings.

DETAILED DESCRIPTION OF THE PREFERRED EMBODIMENTS

The present specification discloses a Photoplethysmography (PPG) front-end receiver, a capacitive transimpedance amplifying device, and a method for sampling a signal. The PPG front-end receiver, the capacitive transimpedance amplifying device, and the method can eliminate an ambient-light signal/noise signal from a detection signal accurately to obtain a controllable-light signal/target signal of the detection signal for analysis and/or utilization.

Figure 1:
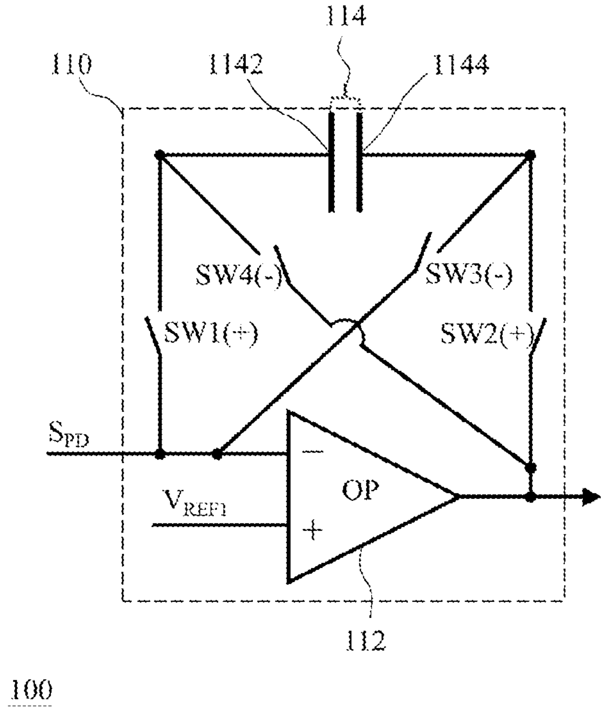
FIG. 1 shows an embodiment of the Photoplethysmography (PPG) front-end receiver of the present disclosure.

FIG. 1 shows an embodiment of the PPG front-end receiver of the present disclosure. The PPG front-end receiver 100 of FIG. 1 can sample a detection signal $S_{PD}$ generated by a photoelectric device (e.g., a photo diode (PD)) (not shown in FIG. 1) multiple times and sampling the inversion of the detection signal $S_{PD}$ multiple times in predetermined sampling sequence (e.g., any of the specific sampling sequences L1, L2, L3, and L4 in FIG. 3) during a sampling period to cancel an ambient-light signal of the detection signal $S_{PD}$ and thereby obtain a controllable-light signal (e.g., an LED light signal) of the detection signal.

Referring to FIG. 1, the PPG front-end receiver 100 includes a first capacitive transimpedance amplifier (CTIA) 110. The first CTIA 110 includes a first operational amplifier (OP) 112, a first capacitor 114, a first switch SW1(+), a second switch SW2(+), a third switch SW3(−), and a fourth switch SW4(−). These circuits are described in detail in the following paragraphs.

Referring to FIG. 1, the first OP 112 includes a first input node, a first inverting input node, and a first output node. The first input node is for receiving a first reference voltage $V_{REF1}$ and the first inverting input node is for receiving the detection signal $S_{PD}$. The first reference voltage $V_{REF1}$ can be determined according to the demand for implementation.

Referring to FIG. 1, the first capacitor 114 includes a first electrode 1142 and a second electrode 1144. The first capacitor 114 can be a capacitor of fixed capacitance or an adjustable capacitor of variable capacitance.

Referring to FIG. 1, the first switch SW1(+) is set between the first electrode 1142 and the first inverting input node, and the second switch SW2(+) is set between the second electrode 1144 and the first output node. The first switch SW1(+) and the second switch SW2(+) are scheduled to be turned on in a first time slot, to be turned off in a second time slot, to be turned off in a third time slot, and to be turned on in a fourth time slot; accordingly, the first electrode 1142 and the second electrode 1144 are coupled with the first inverting input node and the first output node respectively during the first time slot and the fourth time slot so as to allow the first capacitor 114 to sample the detection signal $S_{PD}$ during the first time slot and the fourth time slot. The first time slot, the second time slot, the third time slot, and the fourth time slot are four consecutive time slots included in the sampling period. It is noted that the PPG front-end receiver 100 of FIG. 1 is applied to a PPG device (not shown in the figures) (e.g., a smart watch having a PPG sensor) which includes at least one controllable light source (e.g., an LED) (not shown in the figures), and the controllable light source is turned on and turned off according to a predetermined schedule so that the detection signal $S_{PD}$ includes an controllable-light signal (e.g., an LED light signal) and an ambient light signal during the first and fourth time slots.

Referring to FIG. 1, the third switch SW3(−) is set between the second electrode 1144 and the first inverting input node, and the fourth switch SW4(−) is set between the first electrode 1142 and the first output node. The third switch SW3(−) and the fourth switch SW4(−) are scheduled to be turned off in the first time slot, to be turned on in the second time slot, to be turned on in the third time slot, and to be turned off in the fourth time slot; accordingly, the second electrode 1144 and the first electrode 1142 are coupled with the first inverting input node and the first output node respectively during the second time slot and the third time slot to allow the first capacitor 114 to sample the inversion of the detection signal $S_{PD}$ during the second time slot and the third time slot. It is noted that the aforementioned controllable light source of the PPG device is turned on and turned off according to the predetermined schedule so that the detection signal $S_{PD}$ includes the ambient-light signal but does not include the controllable-light signal during the second time slot and the third time slot.

To sum up, the detection signal $S_{PD}$ includes the controllable-light signal and the ambient-light signal during the first time slot and the fourth time slot, and the first capacitor 114 samples the detection signal $S_{PD}$ during the first time slot and the fourth time slot; the detection signal $S_{PD}$ includes the ambient-light signal but does not include the controllable-light signal during the second time slot and the third time slot, and the first capacitor 114 samples the inversion of the detection signal $S_{PD}$ during the second time slot and the third time slot; and the sum of the signals sampled by the first capacitor 114 during the first, second, third, and fourth time slots is as follows:

(controllable-light signal+ambient-light signal)−(ambient-light signal)−(ambient-light signal)+(controllable-light signal+ambient-light signal)=controllable-light signal+controllable-light signal Accordingly, the ambient-light signal is cancelled and the controllable-light signal is retained.

Figure 2:
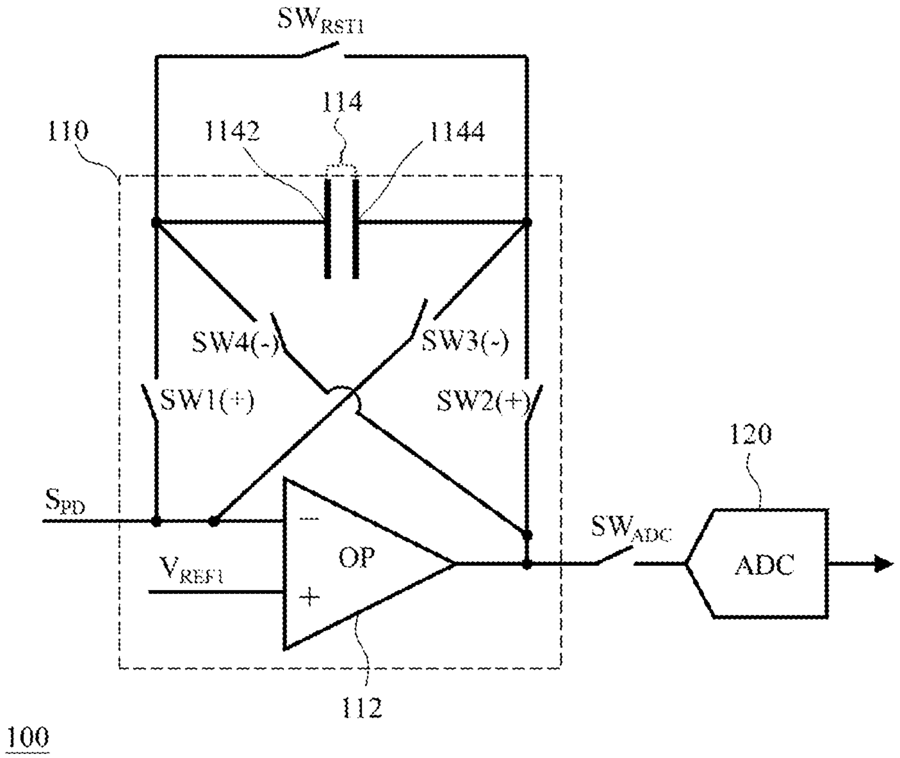
FIG. 2 shows a modification to the embodiment of FIG. 1.

It is noted that the PPG front-end receiver 100 may further include a switch $SW_{ADC}$, an analog-to-digital converter (ADC) 120, and a first reset switch $SW_{RST1}$ as shown in FIG. 2. The switch $SW_{ADC}$ is set between the first output node and the ADC 120, and is turned off during the aforementioned sampling period and turned on during a conversion period which follows the sampling period or is later than the sampling period for an interval. During the conversion period, the ADC 120 converts the output of the first CTIA 110 into a digital value for analysis and/or utilization. The reset switch $SW_{RST1}$ is set between the first electrode 1142 and the second electrode 1144, and is turned off during the sampling period and the conversion period and turned on during a reset period to reset the state of the first capacitor 114, wherein the reset period follows the conversion period or is later than the conversion period for an interval.

Referring to FIG. 1, the PPG front-end receiver 100 can sample the detection signal $S_{PD}$ more times in some circumstances (e.g., a circumstance that the PPG device user exercises strenuously). For example, the first switch SW1(+) and the second switch SW2(+) are further scheduled to be turned off during a fifth time slot, to be turned on during a sixth time slot, to be turned on during a seventh time slot, and to be turned off during an eighth time slot; accordingly, the first electrode 1142 and the second electrode 1144 are coupled with the first inverting input node and the first output node respectively during the sixth time slot and the seventh time slot to allow the first capacitor 114 to sample the detection signal $S_{PD}$ during the sixth time slot and the seventh time slot, wherein the fifth time slot, the sixth time slot, the seventh time slot, and the eighth time slot are another four consecutive time slots following the aforementioned four consecutive time slots and being included in the sampling period. The third switch SW3(−) and the fourth switch SW4(−) are scheduled to be turned on during the fifth time slot, to be turned off during the sixth time slot, to be turned off during the seventh time slot, and to be turned on during the eighth time slot; accordingly, the second electrode 1144 and the first electrode 1142 are coupled with the first inverting input node and the first output node respectively during the fifth time slot and the eighth time slot to allow the first capacitor 114 to sample the inversion of the detection signal $S_{PD}$ during the fifth time slot and the eighth time slot. The aforementioned controllable light source of the PPG device is turned on and turned off according to the predetermined schedule so that: the detection signal $S_{PD}$ includes the controllable-light signal and the ambient-light signal during the sixth time slot and the seventh time slot; and the detection signal $S_{PD}$ includes the ambient-light signal but does not include the controllable-light signal during the fifth time slot and the eighth time slot. In light of the above, the sum of the signals sampled by the first capacitor 114 during the fifth, sixth, seventh, and eighth time slots is as follows:

−(ambient-light signal)+(controllable-light signal+ambient-light signal)+(controllable-light signal+ambient-light signal)−(ambient-light signal)=controllable-light signal+controllable-light signal Accordingly, the ambient-light signal is cancelled and the controllable-light signal is retained.

Figure 3:
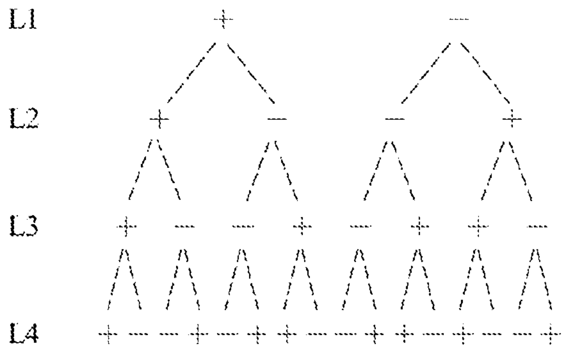
FIG. 3 shows an embodiment explaining how the predetermined sampling sequence is expanded.

FIG. 3 shows an embodiment explaining how the aforementioned predetermined sampling sequence is expanded. Each of the layers L1, L2, L3, and L4 in FIG. 3 stands for a specific sampling sequence that can be used as the predetermined sampling sequence, wherein the (K+1)th layer is the expansion of the $K^{th}$ layer, and the K is a positive integer. Regarding each of the layers L1, L2, L3, and L4: the symbol "+" denotes the detection signal $S_{PD}$ including a controllable-light signal and an ambient-light signal while the first switch SW1(+) and the second switch SW2(+) are turned on and the third switch SW3(−) and the fourth switch SW4(−) are turned off; and the symbol "−" denotes the detection signal $S_{PD}$ including the ambient-light signal without including the controllable-light signal while the first switch SW1(+) and the second switch SW2(+) are turned off and the third switch SW3(−) and the fourth switch SW4(−) are turned on. It is noted that each specific sampling sequence (i.e., each of the layers L1, L2, L3, and L4) in the embodiment of FIG. 3 can ensure that the Fourier Transform result of the sum of the $(2^N-1)^{th}$ sampled signal and the $2^N$ sampled signal obtained by the first capacitor 114 has a response conforming to the form of a sine function in a frequency domain in regard to an ambient light, and this ensures the optimization of the sum of all sampled signals, wherein the N is a positive integer. In brief, other kinds of sampling sequences (e.g., ++−−++−−, . . . , or +−+−+−+− . . . , or +−−++−−+ . . . ) cannot realize the optimization of the sum of all sampled signals.

Figure 4:
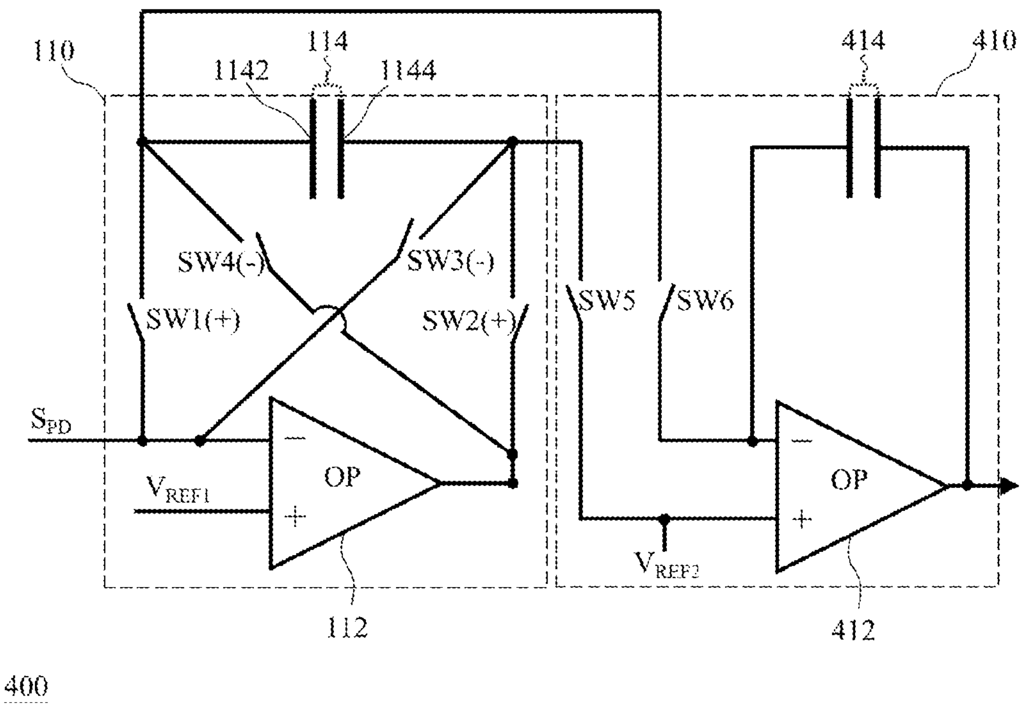
FIG. 4 shows another embodiment of the PPG front-end receiver of the present disclosure.

FIG. 4 shows another embodiment of the PPG front-end receiver of the present disclosure. Compared with FIG. 1, the PPG front-end receiver 400 of FIG. 4 further includes a second CTIA 410 for amplifying the output of the first CTIA 110. The second CTIA 410 includes a second OP 412, a second capacitor 414, a fifth switch SW5, and a sixth switch SW6.

Referring to FIG. 4, the second OP 412 includes a second input node, a second inverting input node, and a second output node. The second input node is coupled with the second electrode 1144 of the first capacitor 114 through the fifth switch SW5 and used for receiving a second reference voltage $V_{REF2}$ The second reference voltage $V_{REF2}$ is the same as or different from the aforementioned first reference voltage $V_{REF1}$, and it can be determined according the demand for implementation. The second inverting input node is coupled with the first electrode 1142 of the first capacitor 114 through the sixth switch SW6.

Referring to FIG. 4, the second capacitor 414 is set between the second inverting input node and the second output node, and the second capacitor 414 and the first capacitor 114 shares charges during a charge sharing period, wherein the capacitance of the second capacitor 414 is less than the capacitance of the first capacitor 114 so that the second CTIA 410 amplifies the output of the first CTIA 110 equivalently, and the charging sharing period follows the sampling period or is later than the sampling period for an interval. In the embodiment of FIG. 4, the capacitance (C1) of the first capacitance is between 150% and 400% of the capacitance (C2) of the second capacitor 414 (i.e., $1.5C2 \leq C1 \leq 4C2$), but the present invention is not limited thereto. The second capacitor 414 can be a capacitor of fixed capacitance or an adjustable capacitor of variable capacitance.

Referring to FIG. 4, the fifth switch SW5 is set between the second electrode 1144 of the first capacitor 114 and the second input node, and the sixth switch SW6 is set between the first electrode 1142 of the first capacitor 114 and the second inverting input node. The fifth switch SW5 and the sixth switch SW6 are scheduled to be turned off during the sampling period and scheduled to be turned on during the charge-sharing period. When the fifth switch SW5 and the sixth switch SW6 are turned on, they are used to electrically connect the first capacitor 114 with the second capacitor 414 and thereby make the first capacitor 114 share charges with the second capacitor 414.

Figure 5:
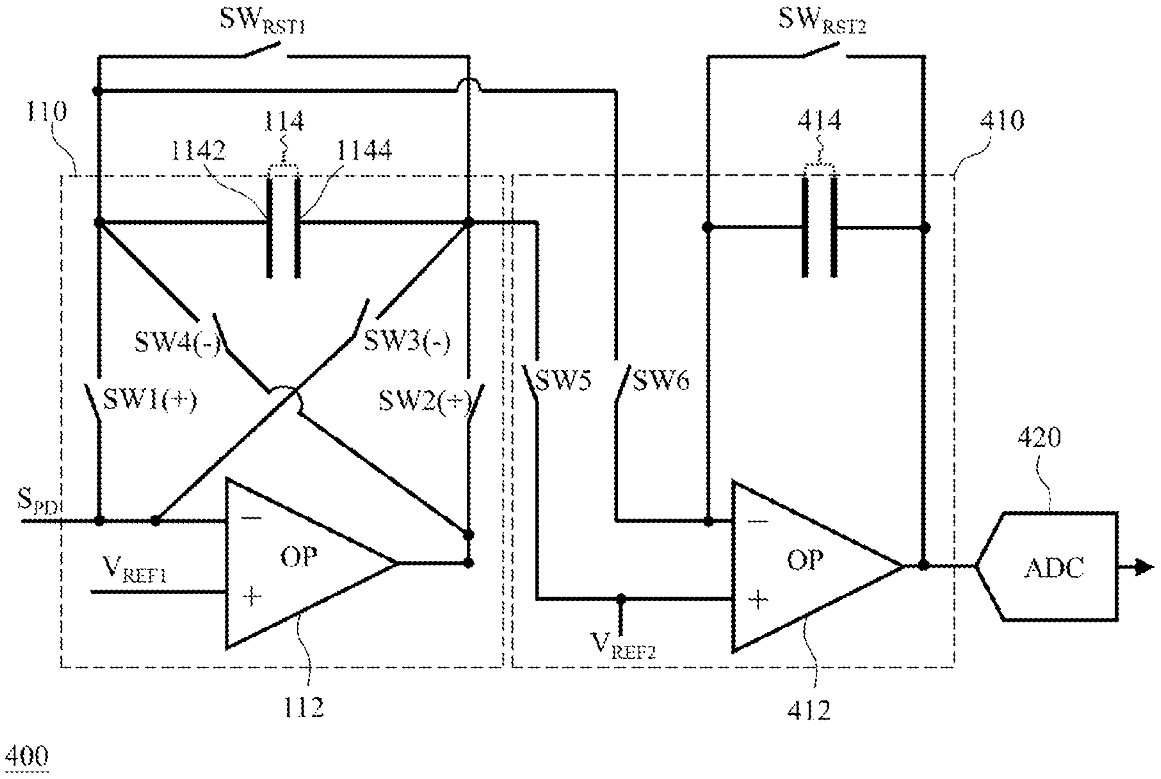
FIG. 5 shows a modification to the embodiment of FIG. 4.

It is noted that the PPG front-end receiver 400 may further include an analog-to-digital converter (ADC) 420, a first reset switch $SW_{RST1}$, and a second reset switch $SW_{RST2}$ as shown in FIG. 5. After the charging sharing period, the ADC 420 is coupled with the second output node and configured to convert the output of the second CTIA 420 into a digital value for analysis and/or utilization. The first reset switch $SW_{RST1}$ is set between the first electrode 1142 and the second electrode 1144 of the first capacitor 114, the second reset switch $SW_{RST2}$ is set between two electrodes of the second capacitor 414, and the first reset switch $SW_{RST1}$ and the second reset switch $SW_{RST2}$ are scheduled to be turned off during the sampling period and the charging sharing period and scheduled to be turned on in a reset period to reset the state of the first capacitor 114 and the state of the second capacitor 414, wherein the reset period follows the operation of the ADC 420 or is later than the operation of the ADC 420 for an interval.

An embodiment of the capacitive transimpedance amplifying device of the present disclosure is the first CTIA 110 of FIG. 1. This embodiment can sample a detection signal multiple times and sample the inversion of the detection signal multiple times in predetermined sampling sequence (e.g., any of the specific sampling sequences L1, L2, L3, and L4 in FIG. 3) during a sampling period to cancel a noise signal of the detection signal and thereby obtain a target signal of the detection signal. This embodiment can be applied to a PPG device or a non-PPG device. Since those having ordinary skill in the art can refer to the embodiments of the FIGS. 1-5 to appreciate the detail and modification of the above embodiment, repeated and redundant description is omitted here.

Figure 6:
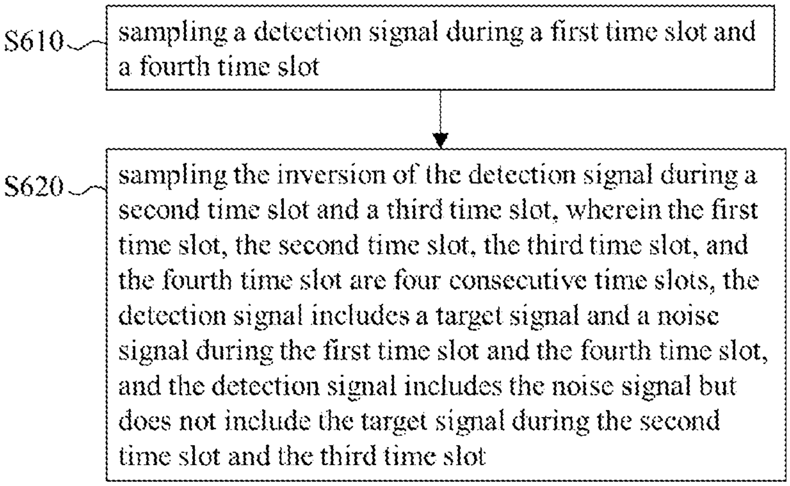
FIG. 6 shows an embodiment of the method of the present disclosure for sampling a signal.

The method of the present disclosure for sampling a signal is performed by a capacitive transimpedance amplifying device (e.g., the first CTIA 110 of FIG. 1). The method is used for sampling a detection signal multiple times and sampling the inversion of the detection signal multiple times in predetermined sampling sequence (e.g., any of the specific sampling sequences L1, L2, L3, and L4 in FIG. 3) during a sampling period to cancel a noise signal of the detection signal and thereby obtain a target signal of the detection signal. FIG. 6 shows an embodiment of the method and includes the following steps:

S610: sampling the detection signal instead of the inversion of the detection signal during a first time slot and a fourth time slot; and

S620: sampling the inversion of the detection signal instead of the detection signal during a second time slot and a third time slot, wherein the first time slot, the second time slot, the third time slot, and the fourth time slot are four consecutive time slots included in the sampling period, the detection signal includes the target signal and the noise signal during the first time slot and the fourth time slot, and the detection signal includes the noise signal but does not include the target signal during the second time slot and the third time slot.

Since those having ordinary skill in the art can refer to the embodiments of the FIGS. 1-5 to appreciate the detail and modification of the embodiment of FIG. 6, repeated and redundant description is omitted here.

It is noted that people having ordinary skill in the art can selectively use some or all of the features of any embodiment in this specification or selectively use some or all of the features of multiple embodiments in this specification to implement the present invention as long as such implementation is practicable; in other words, the way to implement the present invention is flexible based on the present disclosure.

To sum up, the PPG front-end receiver, the capacitive transimpedance amplifying device, and the signal sampling method of the present disclosure can eliminate an ambient-light signal/noise signal from a detection signal accurately and thereby obtain a controllable-light signal/target signal of the detection signal for analysis and/or utilization.

The aforementioned descriptions represent merely the preferred embodiments of the present invention, without any intention to limit the scope of the present invention thereto. Various equivalent changes, alterations, or modifications based on the claims of the present invention are all consequently viewed as being embraced by the scope of the present invention.

What is claimed is:

1. A Photoplethysmography (PPG) front-end receiver, the PPG front-end receiver sampling a detection signal multiple times and sampling an inversion of the detection signal multiple times in predetermined sampling sequence during a sampling period to cancel an ambient-light signal of the detection signal and thereby obtain a controllable-light signal of the detection signal, the detection signal being generated by a photoelectric device, and the PPG front-end receiver comprising:

a first capacitive transimpedance amplifier including:

a first operational amplifier including a first input node, a first inverting input node, and a first output node, wherein the first input node is for receiving a first reference voltage and the first inverting input node is for receiving the detection signal;

a first capacitor including a first electrode and a second electrode;

a first switch set between the first electrode and the first inverting input node;

a second switch set between the second electrode and the first output node, wherein the first switch and the second switch are scheduled to be turned on in a first time slot, to be turned off in a second time slot, to be turned off in a third time slot, and to be turned on in a fourth time slot, the first electrode and the second electrode are coupled with the first inverting input node and the first output node respectively during the first time slot and the fourth time slot to allow the first capacitor to sample the detection signal during the first time slot and the fourth time slot, and the first time slot, the second time slot, the third time slot, and the fourth time slot are four consecutive time slots included in the sampling period;

a third switch set between the second electrode and the first inverting input node; and a fourth switch set between the first electrode and the first output node, wherein the third switch and the fourth switch are scheduled to be turned off in the first time slot, to be turned on in the second time slot, to be turned on in the third time slot, and to be turned off in the fourth time slot, and the second electrode and the first electrode are coupled with the first inverting input node and the first output node respectively during the second time slot and the third time slot to allow the first capacitor to sample the inversion of the detection signal during the second time slot and the third time slot, wherein the detection signal includes the controllable-light signal and the ambient-light signal during the first time slot and the fourth time slot, and the detection signal includes the ambient-light signal but does not include the controllable-light signal during the second time slot and the third time slot.

2. The PPG front-end receiver of claim 1, wherein:

the first switch and the second switch are scheduled to be turned off during a fifth time slot, to be turned on during a sixth time slot, to be turned on during a seventh time slot, and to be turned off during an eighth time slot; the first electrode and the second electrode are coupled with the first inverting input node and the first output node respectively during the sixth time slot and the seventh time slot to allow the first capacitor to sample the detection signal during the sixth time slot and the seventh time slot; and the fifth time slot, the sixth time slot, the seventh time slot, and the eighth time slot are another four consecutive time slots following the four consecutive time slots and being included in the sampling period; and the third switch and the fourth switch are scheduled to be turned on during the fifth time slot, to be turned off during the sixth time slot, to be turned off during the seventh time slot, and to be turned on during the eighth time slot; and the second electrode and the first electrode are coupled with the first inverting input node and the first output node respectively during the fifth time slot and the eighth time slot to allow the first capacitor to sample the inversion of the detection signal during the fifth time slot and the eighth time slot, wherein the detection signal includes the controllable-light signal and the ambient-light signal during the sixth time slot and the seventh time slot, and the detection signal includes the ambient-light signal but does not include the controllable-light signal during the fifth time slot and the eighth time slot.

3. The PPG front-end receiver of claim 1, further comprising a second capacitive transimpedance amplifier, wherein the second capacitive transimpedance amplifier includes:

a second operational amplifier including a second input node, a second inverting input node, and a second output node, wherein the second input node is for receiving a second reference voltage that is the same as or different from the first reference voltage;

a second capacitor set between the second inverting input node and the second output node;

a fifth switch set between the second electrode of the first capacitor and the second input node; and a sixth switch set between the first electrode of the first capacitor and the second inverting input node, wherein the fifth switch and the sixth switch are scheduled to be turned off during the sampling period and scheduled to be turned on during a charge-sharing period to electrically connect the first capacitor with the second capacitor and thereby make the first capacitor share charges with the second capacitor, the charge-sharing period is later than the sampling period, and capacitance of the first capacitor is greater than the capacitance of the second capacitor.

4. The PPG front-end receiver of claim 3, wherein the capacitance of the first capacitor is between 150% of the capacitance of the second capacitor and 400% of the capacitance of the second capacitor.

5. The PPG front-end receiver of claim 3, wherein at least one of the first capacitor and the second capacitor is an adjustable capacitor.

6. The PPG front-end receiver of claim 3, further comprising:

an analog-to-digital converter (ADC) coupled with the second output node and configured to generate a digital value according to an output of the second operational amplifier after the charge-sharing period.

7. The PPG front-end receiver of claim 6, further comprising:

a first reset switch set between the first electrode and the second electrode, and scheduled to be turned on after the ADC outputs the digital value and thereby reset a state of the first capacitor; and a second reset switch set between two electrodes of the second capacitor, and scheduled to be turned on after the ADC outputs the digital value and thereby reset a state of the second capacitor.

8. The PPG front-end receiver of claim 1, wherein the first capacitor is an adjustable capacitor.

9. The PPG front-end receiver of claim 1, further comprising:

an analog-to-digital converter (ADC) coupled with the first output node and configured to generate a digital value according to an output of the first operational amplifier after the sampling period.

10. The PPG front-end receiver of claim 1, further comprising:

a first reset switch set between the first electrode and the second electrode, and scheduled to be turned on after the ADC outputs the digital value and thereby reset a state of the first capacitor.

11. A capacitive transimpedance amplifying device, the capacitive transimpedance amplifying device sampling a detection signal multiple times and sampling an inversion of the detection signal multiple times in predetermined sampling sequence during a sampling period to cancel a noise signal of the detection signal and thereby obtain a target signal of the detection signal, the capacitive transimpedance amplifying device comprising:

a first capacitive transimpedance amplifier including:

a first operational amplifier including a first input node, a first inverting input node, and a first output node, wherein the first input node is for receiving a first reference voltage and the first inverting input node is for receiving the detection signal;

a first capacitor including a first electrode and a second electrode;

a first switch set between the first electrode and the first inverting input node;

a second switch set between the second electrode and the first output node, wherein the first switch and the second switch are scheduled to be turned on in a first time slot, to be turned off in a second time slot, to be turned off in a third time slot, and to be turned on in a fourth time slot, the first electrode and the second electrode are coupled with the first inverting input node and the first output node respectively during the first time slot and the fourth time slot to allow the first capacitor to sample the detection signal during the first time slot and the fourth time slot, and the first time slot, the second time slot, the third time slot, and the fourth time slot are four consecutive time slots included in the sampling period;

a third switch set between the second electrode and the first inverting input node; and a fourth switch set between the first electrode and the first output node, wherein the third switch and the fourth switch are scheduled to be turned off in the first time slot, to be turned on in the second time slot, to be turned on in the third time slot, and to be turned off in the fourth time slot, and the second electrode and the first electrode are coupled with the first inverting input node and the first output node respectively during the second time slot and the third time slot to allow the first capacitor to sample the inversion of the detection signal during the second time slot and the third time slot, wherein the detection signal includes the target signal and the noise signal during the first time slot and the fourth time slot, and the detection signal includes the noise signal but does not include the target signal during the second time slot and the third time slot.

12. The capacitive transimpedance amplifying device of claim 11, wherein the first switch and the second switch are scheduled to be turned off during a fifth time slot, to be turned on during a sixth time slot, to be turned on during a seventh time slot, and to be turned off during an eighth time slot; the first electrode and the second electrode are coupled with the first inverting input node and the first output node respectively during the sixth time slot and the seventh time slot to allow the first capacitor to sample the detection signal during the sixth time slot and the seventh time slot; and the fifth time slot, the sixth time slot, the seventh time slot, and the eighth time slot are another four consecutive time slots following the four consecutive time slots and being included in the sampling period; and the third switch and the fourth switch are scheduled to be turned on during the fifth time slot, to be turned off during the sixth time slot, to be turned off during the seventh time slot, and to be turned on during the eighth time slot; and the second electrode and the first electrode are coupled with the first inverting input node and the first output node respectively during the fifth time slot and the eighth time slot to allow the first capacitor to sample the inversion of the detection signal during the fifth time slot and the eighth time slot, wherein the detection signal includes the target signal and the noise signal during the sixth time slot and the seventh time slot, and the detection signal includes the noise signal but does not include the target signal during the fifth time slot and the eighth time slot.

13. The capacitive transimpedance amplifying device of claim 11, further comprising a second capacitive transimpedance amplifier, wherein the second capacitive transimpedance amplifier includes:

a second operational amplifier including a second input node, a second inverting input node, and a second output node, wherein the second input node is for receiving a second reference voltage that is the same as or different from the first reference voltage;

a second capacitor set between the second inverting input node and the second output node;

a fifth switch set between the second electrode of the first capacitor and the second input node; and a sixth switch set between the first electrode of the first capacitor and the second inverting input node, wherein the fifth switch and the sixth switch are scheduled to be turned off during the sampling period and scheduled to be turned on during a charge-sharing period to electrically connect the first capacitor with the second capacitor and thereby make the first capacitor share charges with the second capacitor, the charge-sharing period is later than the sampling period, and capacitance of the first capacitor is greater than the capacitance of the second capacitor.

14. The capacitive transimpedance amplifying device of claim 13, wherein the capacitance of the first capacitor is between 150% of the capacitance of the second capacitor and 400% of the capacitance of the second capacitor.

15. The capacitive transimpedance amplifying device of claim 13, wherein at least one of the first capacitor and the second capacitor is an adjustable capacitor.

16. The capacitive transimpedance amplifying device of claim 13, further comprising:

an analog-to-digital converter (ADC) coupled with the second output node and configured to generate a digital value according to an output of the second operational amplifier after the charge-sharing period.

17. The capacitive transimpedance amplifying device of claim 16, further comprising:

a first reset switch set between the first electrode and the second electrode, and scheduled to be turned on after the ADC outputs the digital value and thereby reset a state of the first capacitor; and a second reset switch set between two electrodes of the second capacitor, and scheduled to be turned on after the ADC outputs the digital value and thereby reset a state of the second capacitor.

18. A method for sampling a signal, the method performed by a capacitive transimpedance amplifying device and used for sampling a detection signal multiple times and sampling an inversion of the detection signal multiple times in predetermined sampling sequence during a sampling period to cancel a noise signal of the detection signal and thereby obtain a target signal of the detection signal, the method comprising:

sampling the detection signal instead of the inversion of the detection signal during a first time slot and a fourth time slot; and sampling the inversion of the detection signal instead of the detection signal during a second time slot and a third time slot, wherein the first time slot, the second time slot, the third time slot, and the fourth time slot are four consecutive time slots included in the sampling period, the detection signal includes the target signal and the noise signal during the first time slot and the fourth time slot, and the detection signal includes the noise signal but does not include the target signal during the second time slot and the third time slot.

19. The method of claim 18, further comprising:

sampling the inversion of the detection signal instead of the detection signal during a fifth time slot and an eighth time slot; and sampling the detection signal instead of the inversion of the detection signal during a sixth time slot and a seventh time slot, wherein the fifth time slot, the sixth time slot, the seventh time slot, and the eighth time slot are another four consecutive time slots following the four consecutive time slots and being included in the sampling period, the detection signal includes the target signal and the noise signal during the sixth time slot and the seventh time slot, and the detection signal includes the noise signal but does not include the target signal during the fifth time slot and the eighth time slot.

20. The method of claim 18, wherein the target signal is a controllable-light signal and the noise signal is an ambient-light signal.

* * * * *